United States Patent
Sgroi, Jr. et al.

(10) Patent No.: US 11,324,509 B2
(45) Date of Patent: May 10, 2022

(54) SPLINE CRASH CORRECTION WITH MOTOR OSCILLATION

(71) Applicant: Covidien LP, Mansfield, MA (US)

(72) Inventors: Anthony Sgroi, Jr., Wallingford, CT (US); Justin Williams, Southbury, CT (US)

(73) Assignee: COVIDIEN LP, Mansfield, MA (US)

( * ) Notice: Subject to any disclaimer, the term of this patent is extended or adjusted under 35 U.S.C. 154(b) by 137 days.

(21) Appl. No.: 16/793,110

(22) Filed: Feb. 18, 2020

(65) Prior Publication Data
US 2020/0305879 A1   Oct. 1, 2020

Related U.S. Application Data

(60) Provisional application No. 62/825,191, filed on Mar. 28, 2019.

(51) Int. Cl.
*A61B 17/115* (2006.01)
*A61B 90/00* (2016.01)
(Continued)

(52) U.S. Cl.
CPC . *A61B 17/1155* (2013.01); *A61B 2017/00398* (2013.01); *A61B 2017/00734* (2013.01);
(Continued)

(58) Field of Classification Search
CPC ................. A61B 17/1155; A61B 2017/07285
(Continued)

(56) References Cited

U.S. PATENT DOCUMENTS

| | | | | |
|---|---|---|---|---|
| 4,289,133 A | * | 9/1981 | Rothfuss | A61B 17/115 227/175.3 |
| 4,573,468 A | * | 3/1986 | Conta | A61B 17/115 227/179.1 |

(Continued)

FOREIGN PATENT DOCUMENTS

JP     2017053394 A     3/2017

OTHER PUBLICATIONS

International Search Report dated May 19, 2020 and Written Opinion completed May 18, 2020 corresponding to counterpart Int'l Patent Application PCT/US2019/063930.

(Continued)

*Primary Examiner* — Gloria R Weeks

(57) ABSTRACT

A method for obviating spline crash in a surgical stapler that utilizes a motor of the surgical stapler includes oscillating an anvil retainer of the surgical stapler in a first oscillation pattern, oscillating the anvil retainer in a second oscillation pattern that is different from the first oscillation pattern after the first oscillation pattern, and retracting the anvil retainer until an anvil of the surgical stapler is in a clamped position relative to a shell assembly after the second oscillation pattern. Oscillating the anvil retainer in the first oscillation pattern includes oscillating the anvil retainer in a longitudinal direction between extension and retraction with the motor such that the anvil moves towards and away from the shell assembly. Oscillating the anvil retainer in the second oscillation pattern includes moving the anvil towards and away from the shell assembly.

19 Claims, 7 Drawing Sheets

(51) Int. Cl.
*A61B 17/00* (2006.01)
*A61B 17/072* (2006.01)

(52) U.S. Cl.
CPC .............. *A61B 2017/07264* (2013.01); *A61B 2017/07271* (2013.01); *A61B 2090/066* (2016.02); *A61B 2562/0261* (2013.01)

(58) Field of Classification Search
USPC ...................................................... 227/180.1
See application file for complete search history.

(56) References Cited

U.S. PATENT DOCUMENTS

| | | | | |
|---|---|---|---|---|
| 4,776,506 | A * | 10/1988 | Green | A61B 17/115 227/19 |
| 4,957,499 | A * | 9/1990 | Lipatov | A61B 17/115 227/180.1 |
| 5,205,459 | A | 4/1993 | Brinkerhoff et al. | |
| 5,271,543 | A | 12/1993 | Grant et al. | |
| 5,718,360 | A | 2/1998 | Green et al. | |
| 6,258,107 | B1 * | 7/2001 | Balazs | A61B 17/115 227/175.1 |
| 7,032,798 | B2 * | 4/2006 | Whitman | A61B 10/0233 227/175.1 |
| 7,168,604 | B2 * | 1/2007 | Milliman | A61B 17/1114 227/175.1 |
| 7,364,060 | B2 * | 4/2008 | Milliman | A61B 17/068 227/175.1 |
| 7,770,776 | B2 * | 8/2010 | Chen | A61B 17/115 227/180.1 |
| 7,857,187 | B2 | 12/2010 | Milliman | |
| 7,918,377 | B2 * | 4/2011 | Measamer | A61B 17/1155 227/180.1 |
| 7,967,181 | B2 * | 6/2011 | Viola | A61B 17/115 227/180.1 |
| 8,567,655 | B2 * | 10/2013 | Nalagatla | H04B 7/0673 227/175.1 |
| 8,573,464 | B2 * | 11/2013 | Nalagatla | A61B 17/1155 227/179.1 |
| 8,640,940 | B2 * | 2/2014 | Ohdaira | A61B 17/07207 227/175.1 |
| 9,421,013 | B2 * | 8/2016 | Patel | A61B 17/068 |
| 9,833,235 | B2 | 12/2017 | Penna et al. | |
| 10,405,864 | B2 * | 9/2019 | Zhan | A61B 17/1155 |
| 10,542,993 | B2 | 1/2020 | Guerrera et al. | |
| 10,695,069 | B2 * | 6/2020 | Guerrera | A61B 17/00234 |
| 2011/0095067 | A1 * | 4/2011 | Ohdaira | A61B 17/07207 227/175.2 |
| 2011/0278346 | A1 * | 11/2011 | Hull | A61B 17/1155 227/180.1 |
| 2012/0029273 | A1 | 2/2012 | Ostrovsky et al. | |
| 2013/0181035 | A1 * | 7/2013 | Milliman | A61B 17/068 227/180.1 |
| 2014/0175149 | A1 * | 6/2014 | Smith | A61B 90/90 227/175.2 |
| 2015/0173757 | A1 * | 6/2015 | Williams | A61B 17/072 227/180.1 |
| 2016/0000428 | A1 * | 1/2016 | Scirica | A61B 1/00089 227/180.1 |
| 2016/0192934 | A1 | 7/2016 | Williams et al. | |
| 2016/0192938 | A1 | 7/2016 | Sgroi, Jr. | |
| 2016/0310134 | A1 | 10/2016 | Contini et al. | |
| 2016/0310141 | A1 | 10/2016 | Penna et al. | |
| 2018/0233850 | A1 * | 8/2018 | Penna | A61B 17/1155 |
| 2018/0242974 | A1 | 8/2018 | Guerrera et al. | |
| 2018/0353186 | A1 | 12/2018 | Mozdzierz et al. | |
| 2019/0059901 | A1 | 2/2019 | Guerrera et al. | |
| 2019/0290284 | A1 | 9/2019 | Guerrera et al. | |
| 2020/0029970 | A1 | 1/2020 | Wang et al. | |
| 2020/0138441 | A1 * | 5/2020 | Sgroi, Jr. | A61B 17/1155 |

OTHER PUBLICATIONS

International Patent Application No. PCT/US19/63930 filed on Dec. 2, 2019 entitled "RO Processing Completed-Placed in Storage".
U.S. Appl. No. 62/779,718, filed Dec. 14, 2018 entitled Inserts, Splines, and Methods for Reducing and/or Eliminating Spline Crash in Surgical Instruments.
Extended European Search Report dated Aug. 12, 2020 corresponding to counterpart Patent Application EP 20165592.5.

* cited by examiner

SPLINE CRASH CORRECTION WITH MOTOR OSCILLATION

CROSS-REFERENCE TO RELATED APPLICATIONS

This application claims the benefit of and priority to U.S. Provisional Patent Application Ser. No. 62/825,191 filed Mar. 28, 2019, the entire disclosure of which is incorporated by reference herein.

BACKGROUND

1. Technical Field

The present disclosure is directed to circular stapling devices, and more particularly, to powered circular stapling devices with motors that include a spline crash correction algorithm.

2. Discussion of Related Art

Circular stapling devices are utilized by clinicians to apply one or more surgical fasteners, e.g., staples or two-part fasteners, to body tissue for the purpose of joining segments of body tissue together and/or for the creation of an anastomosis. Circular stapling devices generally include a cartridge or shell assembly supporting a plurality of annular rows of staples, an anvil assembly operatively associated with the cartridge assembly and having annular arrays of staple receiving pockets for providing a surface against which the plurality of annular rows of staples can be formed, and an annular blade for cutting tissue.

During a typical tissue fastening procedure, the anvil assembly of the stapling device is positioned within one segment of body tissue and the shell assembly and a body portion of the stapling device supporting the shell assembly are positioned in an adjacent segment of body tissue. The anvil assembly is then attached to the body portion of the stapling device and the stapling device is actuated to approximate the anvil assembly with a staple cartridge of the shell assembly and clamp the body tissue segments together.

Typically, the anvil assembly includes an anvil shaft that includes splines that mate with splines formed within a shell housing of the shell assembly to align the staple forming pockets of the anvil assembly with staple receiving pockets of the staple cartridge of the shell assembly. The splines on the anvil shaft and on the shell housing of the shell assembly include left and right tapered ends that define an apex. When the right tapered ends of the splines of the anvil assembly engage the left tapered ends of the shell assembly (or vice versa), the anvil assembly will be rotated to allow the splines of the anvil assembly to pass between the splines of shell assembly to align the anvil assembly with the shell assembly. However, if the right tapered end of one spline of the anvil assembly engages the right tapered end of one spline of the shell assembly and a left tapered end of another spline of the anvil assembly engages the left tapered end of another spline of the shell assembly, or if the apexes of the splines of the anvil assembly and the shell assembly simultaneously hit head on, i.e., crash, the splines of the anvil assembly and the shell assembly may be damaged and/or the anvil assembly and the shell assembly may bind such that approximation of the anvil and shell assemblies is prevented or malformation of the staples may occur during firing of the stapling device.

A continuing need exist for circular stapling devices that mitigate or prevent spline crash to more reliably align the staple forming pockets of the anvil assembly with the staple receiving pockets of the staple cartridge of the shell assembly.

SUMMARY

This disclosure relates generally methods of oscillating an anvil assembly of a surgical stapler relative to a shell assembly of the surgical stapler when spline crash is detected to rotate the anvil assembly relative to the shell assembly to obviate the spline crash.

In an aspect of the present disclosure, a method for obviating spline crash in a surgical stapler that utilizes a motor of the surgical stapler includes oscillating an anvil retainer of the surgical stapler in a first oscillation pattern, oscillating the anvil retainer in a second oscillation pattern that is different from the first oscillation pattern after the first oscillation pattern, and retracting the anvil retainer until an anvil of the surgical stapler is in a clamped position relative to a shell assembly after the second oscillation pattern. Oscillating the anvil retainer in the first oscillation pattern includes the motor oscillating the anvil retainer in a longitudinal direction between extension and retraction such that the anvil moves towards and away from the shell assembly. Oscillating the anvil retainer in the second oscillation pattern includes the motor moving the anvil towards and away from the shell assembly.

In aspects, oscillating the anvil retainer in the first oscillation pattern includes cycling the motor between extending the anvil retainer a first distance and then retracting the anvil retainer the first distance. Oscillating the anvil retainer in the first oscillation pattern may include cycling the motor in a range of about 5 to about 20 cycles before oscillating the anvil retainer in the second oscillation pattern. Oscillating the anvil retainer in the second oscillation pattern may include cycling the motor between extending the anvil retainer a second distance and then retracting the anvil retainer a third distance that is greater than the second distance. Oscillating the anvil retainer in the second oscillation pattern may include cycling the motor in a range of about 5 to about 10 cycles before retracting the anvil retainer until the anvil is in the clamped position. Oscillating the anvil retainer in the second oscillation pattern may include cycling the motor half of the number of cycles as the number of cycles the motor is cycled during oscillating the anvil retainer in the first oscillation pattern.

In some aspects, the third distance is equal to the first distance. The second distance may be half of the third distance. Oscillating the motor in the first oscillation pattern may include cycling the motor at a frequency in a range of about 0.25-5 Hz.

In certain aspects, oscillating the anvil retainer in the first oscillation pattern includes cycling the motor to extend the anvil retainer for a first time period and then to retract the anvil retainer for a second time period equal to the first time period. Oscillating the anvil retainer in the second oscillation pattern may include cycling the motor to retract the anvil retainer for a fourth time period that is greater than the third time period. The third time period may be half of the fourth time period. The fourth time period may be equal to the first time period.

In particular aspects, oscillating the motor in the first oscillation pattern and oscillating the motor in the second oscillation pattern may include cycling the motor at the same frequency.

In aspects, the method includes detecting potential spline crash of an anvil spline of an anvil assembly of the surgical stapler with a shell spline of the shell assembly of the surgical stapler before oscillating the anvil retainer in the first oscillation pattern. The method may include detecting potential spline crash of the anvil spline with the shell spline after oscillating the anvil retainer in the first oscillation pattern and repeating oscillating the anvil retainer in the first oscillation pattern.

In another aspect of the present disclosure, the method for obviating spline crash in a surgical stapler utilizing a motor of the surgical stapler includes oscillating an anvil retainer in a first oscillation pattern and retracting the anvil retainer until the anvil is in a clamped position relative to a shell assembly after the first oscillation pattern. Oscillating the anvil retainer in the first oscillation pattern includes utilizing a motor to extend and retract an anvil retainer such that the anvil of the surgical stapler moves towards and away from the shell assembly of the surgical stapler in the first oscillation pattern.

In some aspects, oscillating the anvil retainer in the first oscillation pattern includes cycling the motor between extension and retraction for about 10 to about 20 cycles.

In another aspect of the present disclosure, a surgical stapler includes an anvil assembly having an anvil spline, a shell assembly having a shell spline, and a handle assembly having an anvil retainer. The shell assembly is secured to a distal portion of the handle assembly and the anvil assembly is secured to the anvil retainer. The handle assembly includes a motor that is configured to extend and retract the anvil retainer through the shell assembly such that the anvil assembly is moved away and towards the shell assembly. The motor is configured to oscillate the anvil retainer between extension and retraction in a first oscillation pattern to obviate a spline crash between the anvil spline and the shell spline.

In aspects, the motor is configured to oscillation the anvil retainer between extension and retraction in a second oscillation pattern that is different form the first oscillation pattern to resume retraction of the anvil assembly relative to the shell assembly after the first oscillation pattern.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
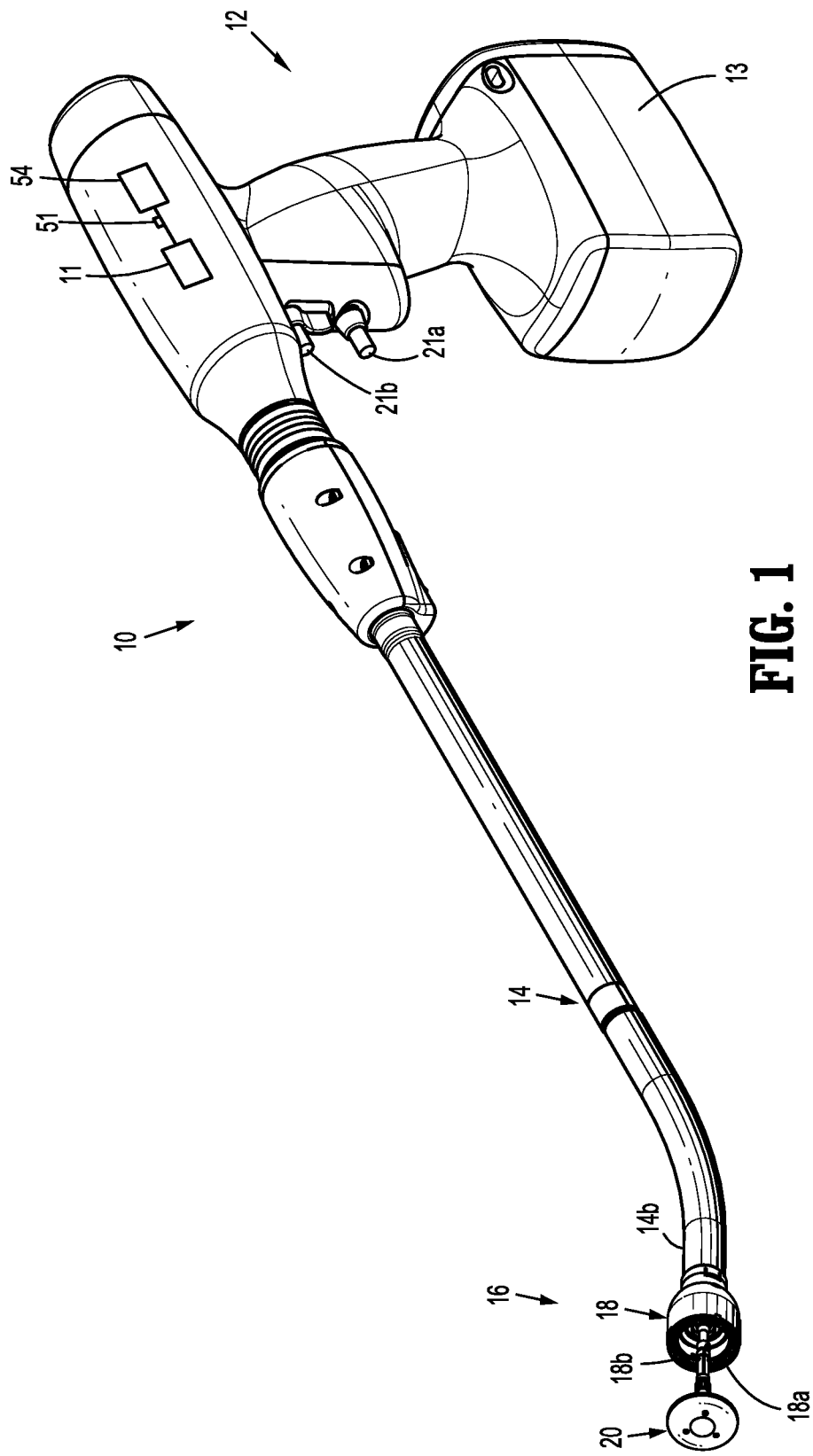
FIG. 1 is a side perspective view of an exemplary embodiment of the presently disclosed surgical stapling device with a tool assembly in a clamped position.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closer to the clinician and the term "distal" refers to the portion of the device or component thereof that is farther from the clinician. In addition, the term "endoscopic" is used generally to refer to endoscopic, laparoscopic, arthroscopic, and/or any other procedure conducted through small diameter incision or cannula.

Figure 2:
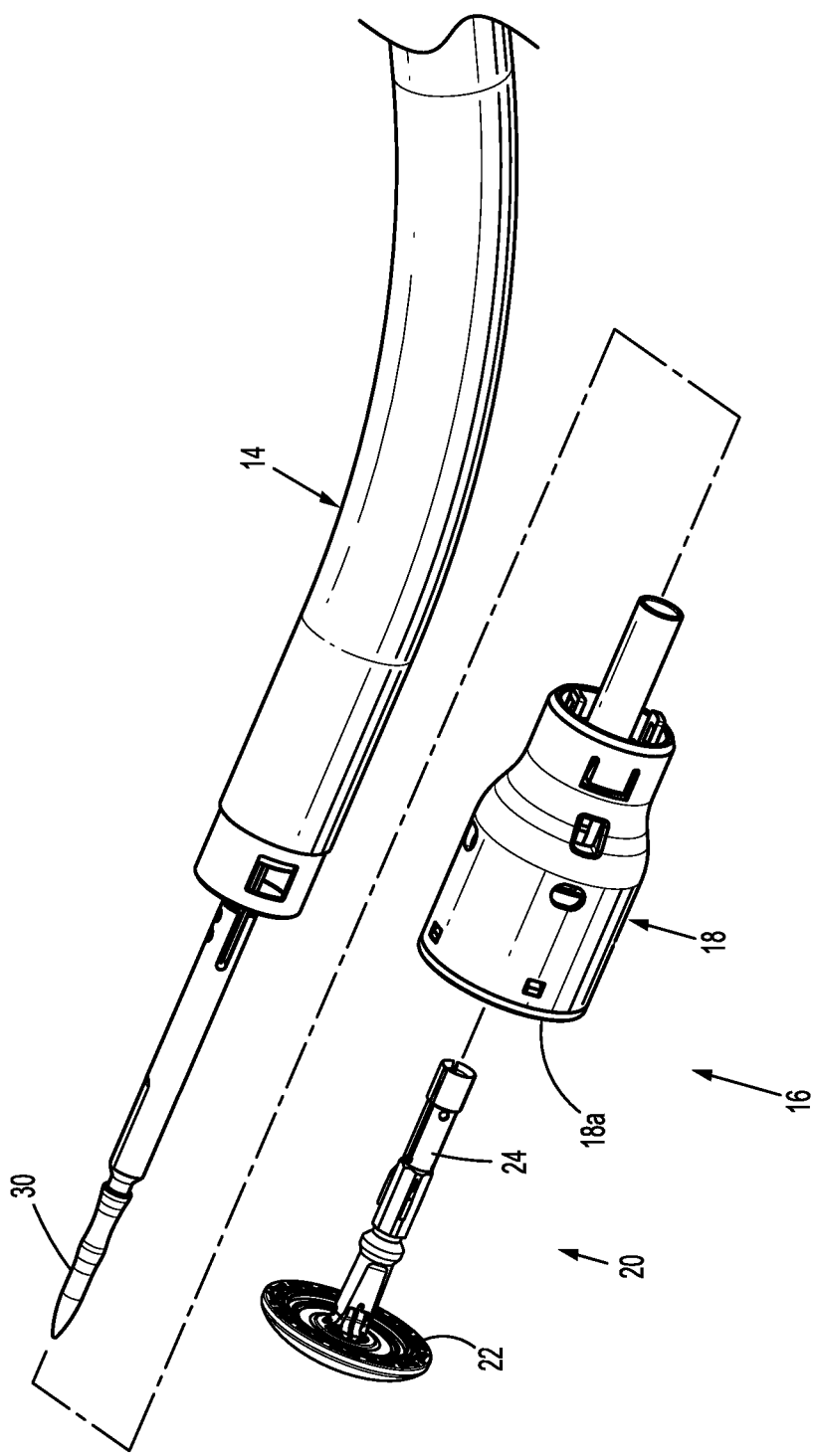
FIG. 2 is a side perspective view of a portion of the surgical stapling device shown in FIG. 1 with a shell assembly of the tool assembly and an anvil assembly of the tool assembly separated from the remaining portion of the stapling device.

Referring to FIGS. 1 and 2, the presently disclosed surgical stapling device shown generally as 10 includes a handle assembly 12, an elongated body portion 14 that extends distally from the handle assembly 12, and a tool assembly 16 that is supported on a distal portion of the elongated body portion 14. The tool assembly 16 includes a cartridge or shell assembly 18 that supports a staple cartridge 18a and an anvil assembly 20 that supports an anvil 22. The handle assembly 12 includes a processing unit or controller 54 in communication with an approximation control 21a to activate a motor 11 to move the anvil assembly 20 between unclamped or spaced-apart and clamped positions in relation to the cartridge assembly 18, a firing control 21b to activate a firing mechanism (not shown) to fire staples (not shown) from the staple cartridge 18a into tissue, and a battery 13 that provides power to the handle assembly 12 including the motor 11 and the processing unit 54. For a detailed description of an exemplary circular stapling device reference can be made to U.S. Pat. No. 9,833,235 ("the'235 Patent"), the entire contents of which are hereby incorporated by reference.

The staple cartridge 18a of the shell assembly 18 and the anvil 22 of the anvil assembly 20, have an annular configuration. The anvil assembly 20 is movable in relation to the shell assembly 18 from a spaced position to a clamped position to move the anvil 22 into juxtaposed alignment with the staple cartridge 18a. The staple cartridge 18a defines staple receiving slots 18b that are aligned with staple deforming recesses (not shown) of the anvil 22 when the staple cartridge 18a and the anvil 22 are properly aligned such that staples ejected from the staple receiving slots 18b are deformed within the staple receiving recesses when the stapling device 10 is fired.

The anvil assembly 20 is supported on an anvil retainer 30 (FIG. 2) which forms part of an approximation mechanism (not shown) of the stapling device 10. The anvil retainer 30 is configured to releasably engage the anvil assembly 20. The anvil retainer 30 includes a distal portion and a proximal portion. The distal portion of the anvil retainer 30 extends from a distal end of the elongate body portion 14 of the stapling device 10 and through the shell assembly 18 to a position to engage the anvil assembly 20. The proximal portion of the anvil retainer 30 is operatively connected to the motor 11 such that activation of the approximation control 21a causes the anvil retainer 30 to move within the shell assembly 18 to move the anvil assembly 20 in relation to the staple cartridge 18a between the spaced position and the clamped position. The shell assembly 18 includes an annular knife (not shown) that is movable from a retracted position to an advanced position within the shell assembly 18 during firing of the stapling device 10 to transect tissue clamped between the staple cartridge 18a and the anvil 22.

Referring to FIG. 2, the shell assembly 18 is releasably coupled to a distal portion of the elongated body 14 of the stapling device 10 to facilitate replacement of the shell assembly 18 after each firing of the stapling device 10. Examples of mechanisms for releasably coupling the shell assembly 18 to the elongate body portion 14 of the stapling device 10 are described in U.S. Patent Publication Nos. 2016/0310141, 2016/0192938, and 2016/0192934. The entire disclosure of each of these publications is hereby incorporated by reference.

Figure 3:
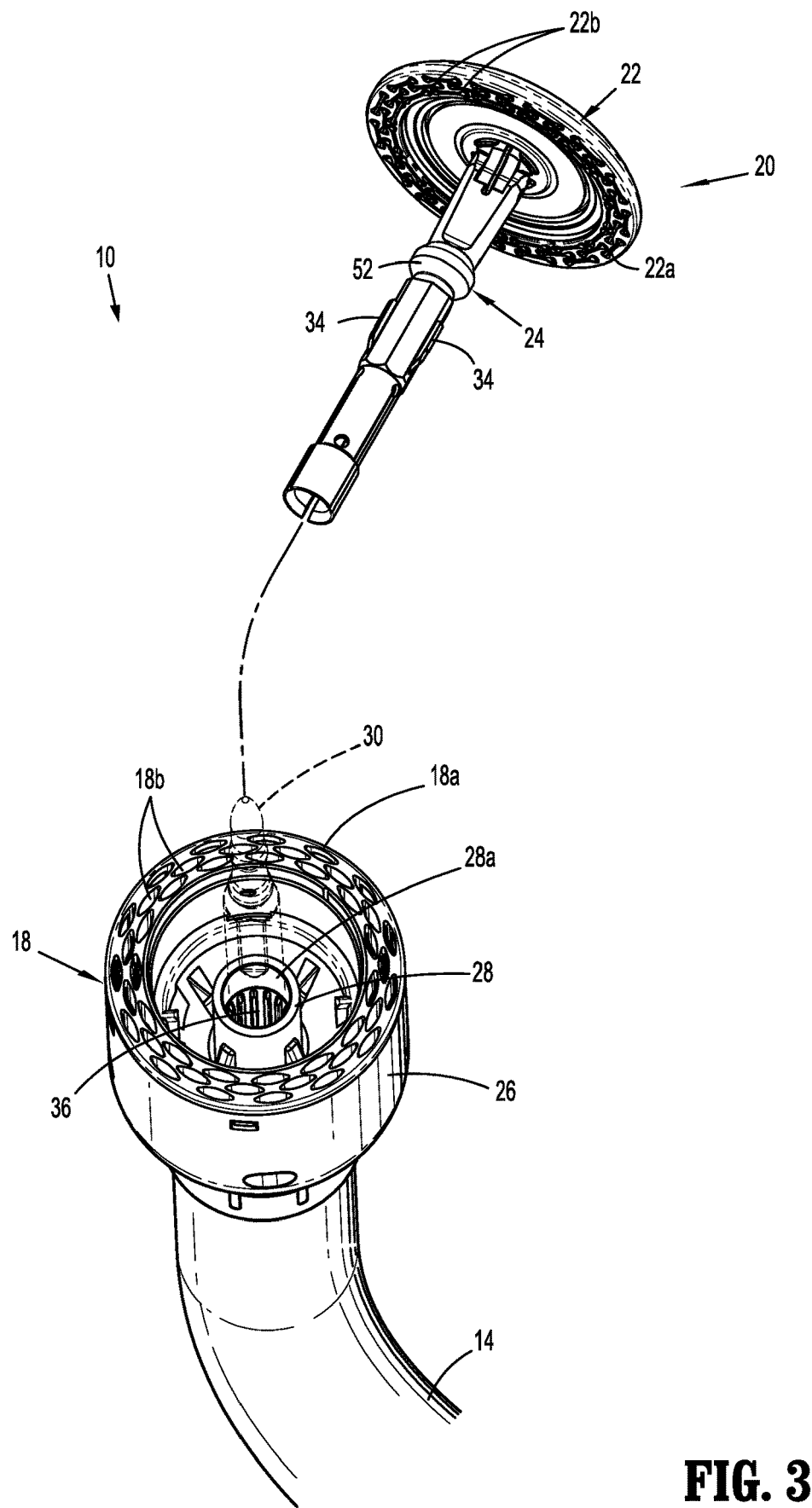
FIG. 3 is a perspective view from a distal end of the surgical stapling device of FIG. 1 with the anvil assembly of the tool assembly of the surgical stapling device separated from an anvil retainer (shown in phantom) of the surgical stapling device.

Referring to FIG. 3, the anvil assembly 20 includes an anvil head 22 and an anvil shaft 24 and the shell assembly 18 includes a shell housing 26 having an inner housing portion 28 that defines a through bore 28a. The anvil head 22 supports an anvil 22a that defines annular arrays of staple deforming recesses 22b and the staple cartridge 18a defines annular arrays of staple receiving slots 18b. An anvil retainer 130 (shown in phantom) includes a distal end that is configured to releasably engage the anvil shaft 24 of the anvil assembly 20. The anvil retainer 30 is received within the through bore 28a and is movable between retracted and advanced positions. When the anvil shaft 24 is coupled to the anvil retainer 30 and the anvil retainer 30 is retracted (via the motor 11, FIG. 1), the anvil shaft 24 is drawn into the through bore 28a of the inner housing portion 28 of the shell housing 26.

Figure 4:
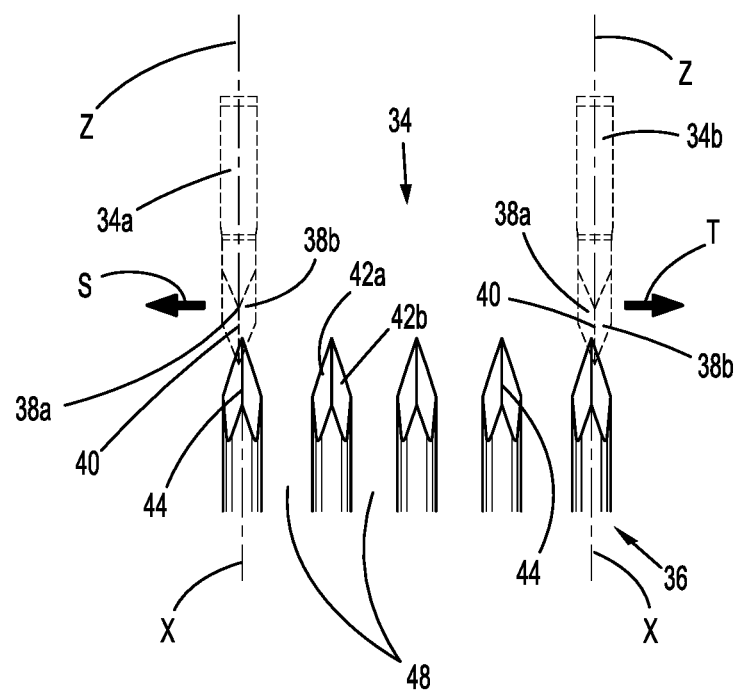
FIG. 4 is a schematic view of a spline configuration of the anvil assembly of the surgical stapling device shown in FIG. 1.

In order to align the arrays of staple deforming recesses 22b of the anvil head 22 of the anvil assembly 20 with the staple receiving slots 18b of the staple cartridge 18a of the shell assembly 18, the anvil shaft 24 includes a plurality of anvil splines 34 including adjacent anvil splines 34a, 34b (FIG. 4) that are received within guide channels 48 defined between adjacent shell splines 36 formed along an inner wall of the inner housing portion 28 of the shell housing 26. Each of the anvil splines 34 of the anvil assembly 20 defines a central axis "Z" and left and right tapered cam surfaces 38a, 38b positioned on opposite sides of the central axis "Z" as viewed in FIG. 4. The tapered surfaces 38a, 38b meet at their proximal ends at an apex 40. Similarly, each of the shell splines 36 of the shell assembly 18 defines a central axis "X" and left and right tapered cam surfaces 42a, 42b positioned on opposite sides of the central axis "X". The tapered surfaces 42a, 142b meet at their distal ends at an apex 44.

When the anvil assembly 20 is attached to the anvil retainer 30 and the anvil retainer 30 and anvil assembly 20 are retracted into the through bore 128a (FIG. 3) of the inner housing portion 28 of the shell housing 26, the anvil splines 34 of the anvil assembly 20 move towards the shell splines 36 of the shell assembly 18. If the anvil splines 34 are misaligned with channels 48 defined between the shell splines 36 of the shell assembly 18, the apexes 40 of the anvil splines 34a, 34b will engage one of the cam surfaces 42a, 42b of the shell splines 36 to rotate or "clock" the anvil assembly 20 relative to the shell assembly 18. When all of the apexes 40 of all of the anvil splines 34a, 34b (only two are shown) engage the left tapered cam surface 42a of the shell splines 36, the engagement urges or cams the anvil assembly 20 to rotate in the direction indicated by arrow "S" to realign the anvil splines 34a, 34b so that they enter into the channels 48 defined between the shell splines 36 of the shell assembly 18. Similarly, when all of the apexes 40 of all of the anvil splines 34a, 34b engage the right tapered cam surface 42b of the shell splines 36, the engagement urges or cams the anvil assembly 20 to rotate in the direction indicated by arrow "T" to clock the anvil shaft 24 to realign the anvil splines 34a, 34b so that they enter into the channels 48 defined between the shell splines 36 of the shell assembly 18. However, if the apexes 40 of any two of the anvil splines 34a, 34b simultaneously engage the left and right tapered cam surfaces 42a, 42b of the two shell splines 36 of the shell assembly 18, the engagement simultaneously urges or cams the anvil assembly 20 in opposite directions. When this happens, the anvil splines 34a, 34b and the shell splines 36 may bind until one or both of the anvil splines 34 and/or the shell splines 36 fractures. In addition, if the apexes 40 of the anvil splines 34a, 34b are aligned with the apexes 44 of the shell splines 36, the apexes may crash into each other causing damage to the anvil splines 34a, 34b and/or shell splines 36. When the anvil splines 34 and 36 crash into or bind with each other and proper alignment between staple receiving recesses 27 of the anvil assembly 20 and staple receiving slots 28 of the shell assembly 18 is not achieved, improper staple formation or locking of the stapling device 10 may result.

It is contemplated that the shell assembly 18 and/or the anvil assembly 20 may be designed and/or include features to reduce the possibility of spline crash and/or reduce the impact of spline crash. Examples of exemplary designs and features are disclosed in U.S. Provisional Patent Application Ser. No. 62/549,266 entitled "CIRCULAR STAPLING DEVICE WITH OFFSET SPLINE TIP," (now U.S. Patent Publication No. 2019/0059901), and 62/779,718 entitled "INSERTS, SPLINES, AND METHODS FOR REDUCING AND/OR ELIMINATING SPLINE CRASH IN SURGICAL INSTRUMENTS," U.S. patent application Ser. No. 15/441,296 entitled "ANVIL ASSEMBLY OF CIRCULAR STAPLING DEVICE INCLUDING ALIGNMENT SPLINES," 15/441,994 entitled "TOOL ASSEMBLY INCLUDING AXIALLY SPACED SPLINES," and 15/935,260 entitled "CIRCULAR STAPLING DEVICE WITH A-FRAME SPLINES," and International Patent Application No. PCT/CN2017/077862 entitled "CIRCULAR STAPLING DEVICE WITH ALIGNMENT SPLINES." The entire disclosure of each of these applications is hereby incorporated by reference.

Figure 5:
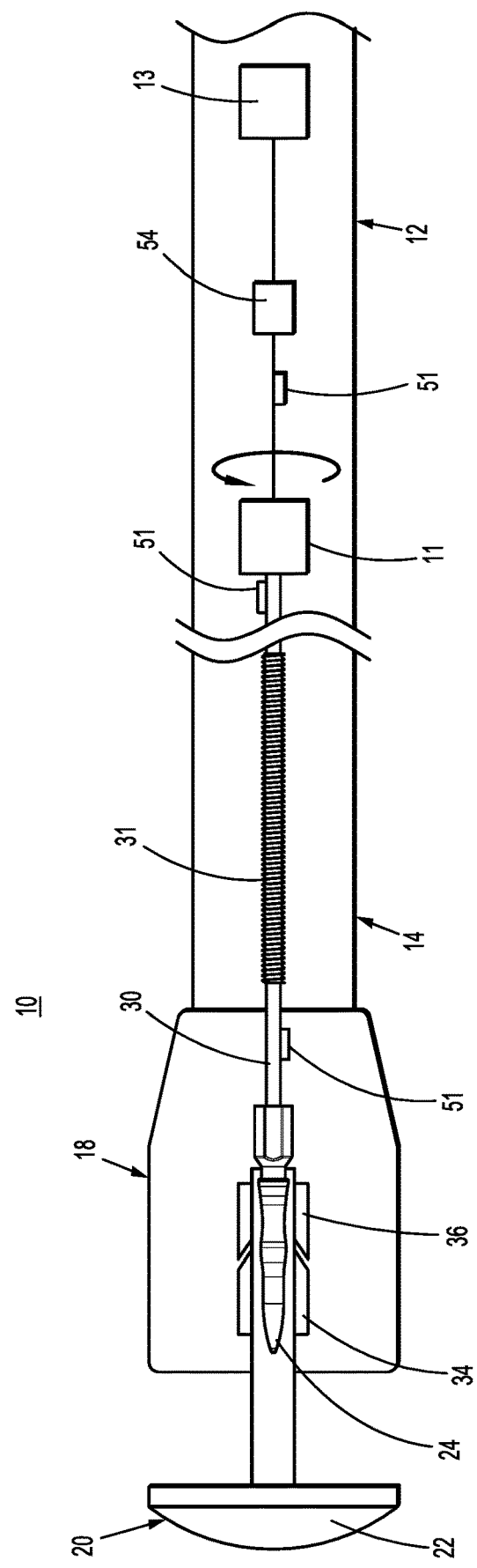
FIG. 5 is a schematic side view of the surgical stapling device of FIG. 1.

With reference to FIG. 5, the motor 11 is operably coupled to a retainer driver 31 that is coupled to the anvil retainer 30. The retainer driver 31 extends and retracts the anvil retainer 30 through the shell assembly 18. In embodiments, the retainer driver 31 is a power screw that is operably coupled to the motor 11. When the anvil retainer 30 is coupled to the anvil shaft 24, the anvil shaft 24, and thus the anvil head 22, cooperates with the extension and the retraction of the anvil retainer 30 to move the anvil assembly 20 between the spaced-apart and approximated positions.

The stapling device 10 includes one or more sensors 51 in communication with the processing unit 54 to determine a clamping force of the anvil retainer 30. For example, a sensor 51 may be disposed in the handle assembly 12 between the motor 11 and the battery 13 (FIG. 1) to determine an amount of power supplied to the motor 11. Another sensor 51 may be operably coupled to the motor 11 to measure a torque of the motor 11. Further, another sensor 51 may be a strain gauge disposed on the anvil retainer 30 to determine strain of the anvil retainer 30.

In use, when the approximation control 21a is actuated, the motor 11 is activated to rotate in a first direction, e.g., clockwise, to retract the anvil retainer 30. While the motor 11 is activated, the sensors 51 determine the clamping force exerted by the anvil retainer 30. In embodiments, the motor 11 is a linear actuator that is operably coupled to the anvil retainer 30. When the anvil shaft 24 is coupled to the anvil retainer 30, the anvil retainer 30 draws the anvil shaft 24 into the bore 28a (FIG. 3) of the shell assembly 18. The clamping force may vary as a result of resistance of the anvil shaft 24 and/or the anvil head 22. For example, as the anvil head 22 moves through and/or compresses tissue between the anvil head and the shell assembly 18, the clamping force may increase and decrease. In addition, when the anvil splines 34 engage the shell splines 36, the clamping force may increase. Further, in the case of spline crash, as detailed above including straddling, the clamping force will increase significantly.

The processing unit 54 monitors the clamping force to detect spline crash. Specifically, when the clamping force exceeds a predetermined threshold, the processing unit 54 determines that spline crash is occurring. When the clamping force exceeds the predetermined threshold, the processing unit 54 begins a spline crash correction algorithm (Crash Algorithm) to prevent a spline crash and to reduce or eliminate damage from a spline crash. The predetermined threshold may be set by the manufacturer or may be selectable by the clinician. The predetermined threshold is set above a clamping force to overcome normal frictional forces between the shell assembly 18 and the anvil assembly 20 and the compressing of tissue between the anvil head 22 and the shell assembly 18.

Figure 6:
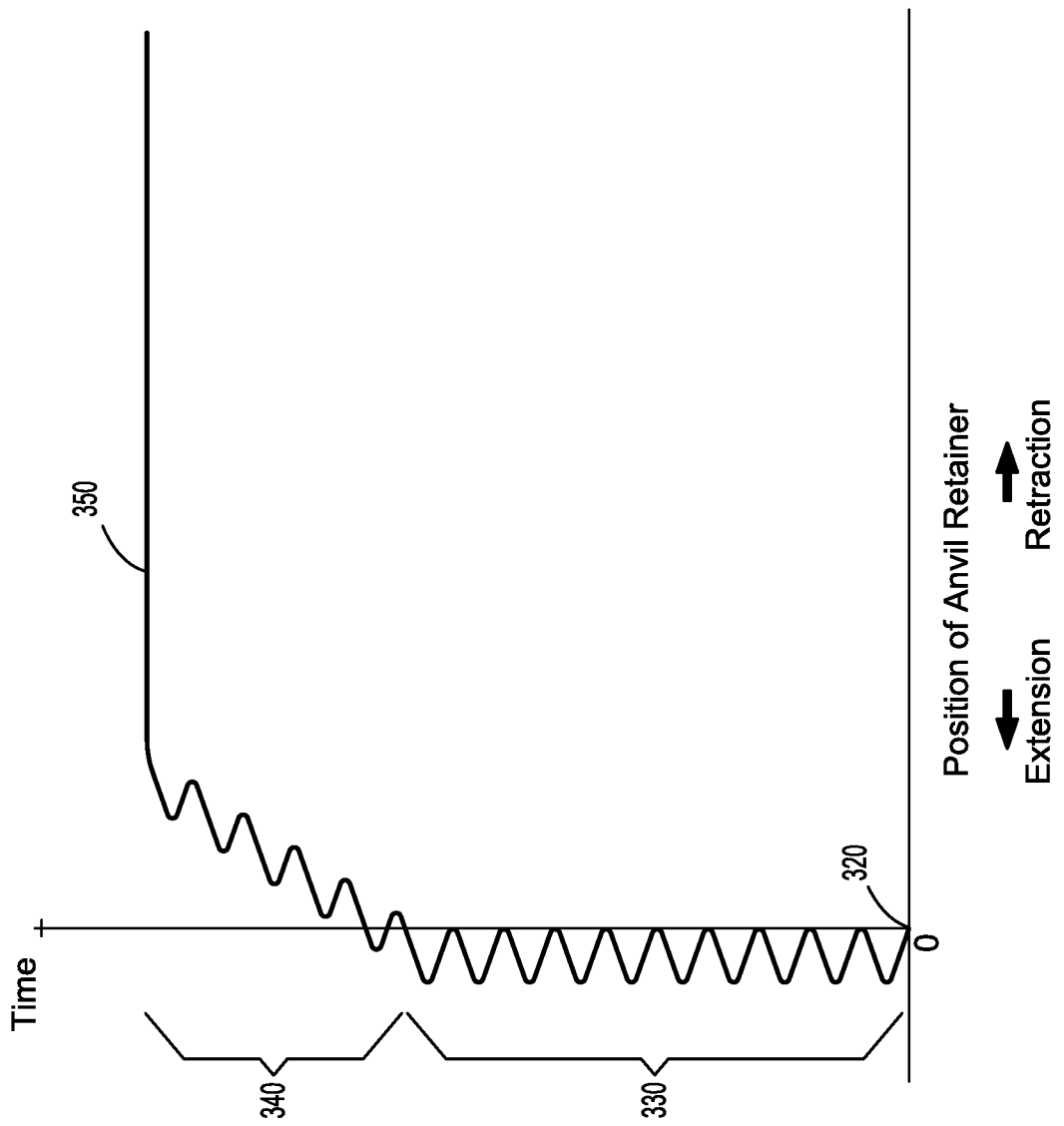
FIG. 6 is a graph of the position of the anvil retainer over time during implementation of a crash algorithm in accordance with the present disclosure.
Figure 7:
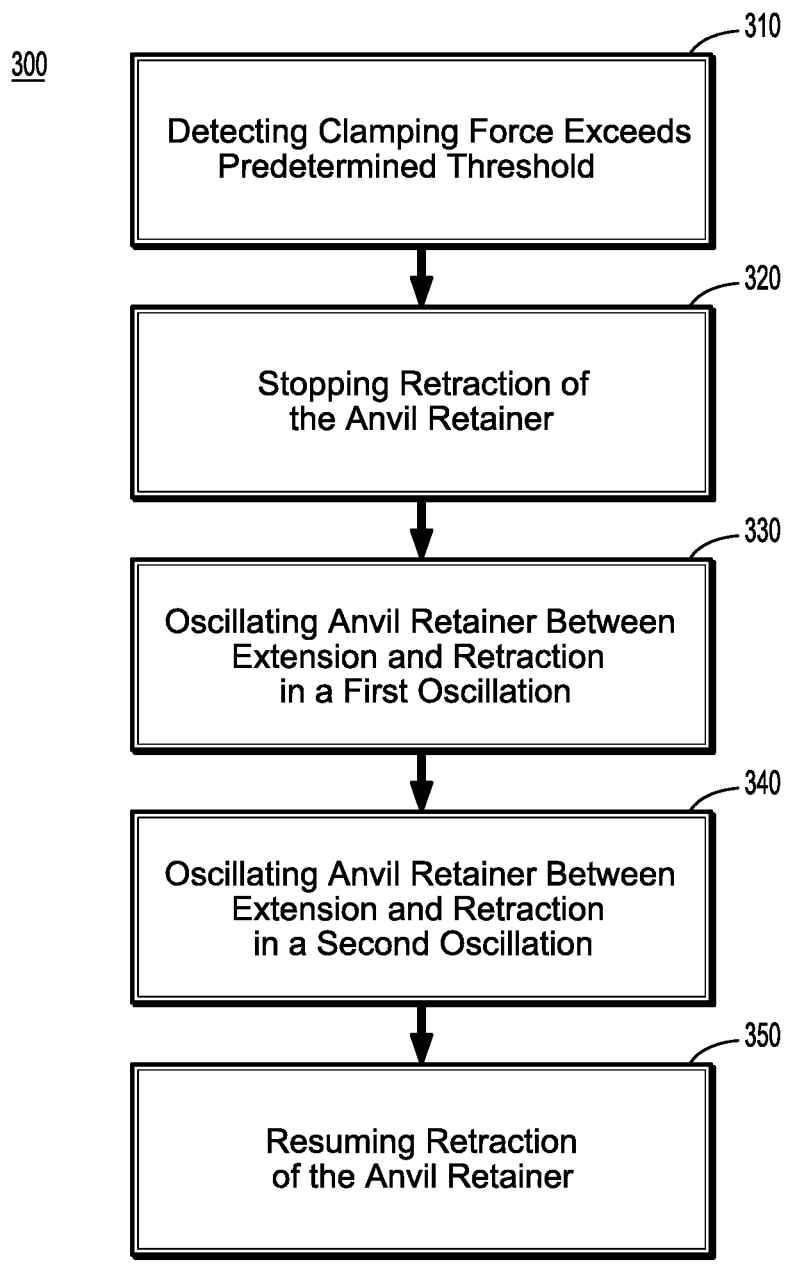
FIG. 7 is a flowchart of the crash algorithm employed to generate the graph of FIG. 6.

With additional reference to FIGS. 6 and 7, the Crash Algorithm 300 is detailed in accordance with the present disclosure with respect to a position of the anvil retainer 30 within the bore 28a (FIG. 3) of the shell assembly 18. Initially, when the clamping force exceeds the predetermined threshold (Step 310). The intersection of the Time and the Position axes is the time at which the clamping force exceeds the predetermined threshold and the position of the anvil retainer 30 at which the clamping force exceeds the predetermined threshold such that the Crash Algorithm is run. As soon as the clamping force exceeds the predetermined threshold, the processing unit 54 stops the motor 11 to stop retraction of the anvil retainer 30 (Step 320). By immediately stopping retraction of the anvil retainer 30, damage from an actual or potential spline crash may be prevented.

Once retraction of the anvil retainer 30 is stopped, the processing unit 54 sends control signals to the motor 11 for a first oscillation (Step 330) to oscillate between a first or retraction direction, e.g., clockwise, and a second or extension direction, e.g., counter-clockwise, beginning with the second direction. During the first oscillation, the amount of oscillation in the first and second directions are approximately equal to one another. For example, the motor 11 may rotate in the second direction by 1 degree and then rotate in the first direction by 1 degree and repeating this oscillation and a predetermined frequency. Without wishing to be bound to a specific frequency, it has been observed that 5 oscillation per second (5 hertz) for 5 seconds produces the amount of movement or controlled vibration necessary to allow for movement of the interfering splines resulting in self-alignment of the splines. The frequency of the first oscillation may slightly rotate the anvil shaft 24 relative to the shell assembly 18 to misalign the apexes 40 (FIG. 4) of the anvil shaft 24 from the apexes 44 (FIG. 4) of the shell splines 36 such that spline crash is prevented. The first oscillation period can be maintained and define a first time-period.

It will be appreciated that by first extending the anvil retainer 30 and then quickly retracting the anvil retainer 30, a small rotation of the anvil shaft 24 may be induced such that the anvil shaft 24 rotates such that the apexes 40 of the anvil splines 34 are rotated to be offset from the apexes 44 of the shell splines 36 such that spline crash is obviated.

After the first oscillation, the processing unit 54 sends control signals to the motor 11 for a second oscillation (Step 340) to oscillate the anvil retainer 30 while beginning to gradually resume retracting the anvil retainer 30. During the second oscillation, the amount of each oscillation in the first direction is greater than the amount of each oscillation in the second direction. For example, the motor 11 may rotate in the second direction by 1 degree and then rotate in the first direction by 1.5 degrees such that each oscillation of the second oscillation results in 0.5 degrees of rotation of the motor 11 towards retraction. The second oscillation is occurs at about the same frequency of the first oscillation or may occur at a slightly slower frequency to account for the additional movement in the first direction. It is contemplated that the amount of oscillation in the first direction may be equal during each oscillation of the second oscillation or may increase for each subsequent oscillation. This increase in amount of oscillation may be linear or exponential. The second oscillation gradually begins to retract the anvil retainer 30 to assist in avoiding spline crash and to reduce initial engagement between the anvil splines 34 and the shell splines 36.

During the first and second oscillations, the clamping force is monitored to ensure that the clamping force does not exceed the predetermined threshold. If the clamping force exceeds the predetermined threshold during the first oscillation, the motor 11 may be rotated in the second direction an extra amount, e.g., about 0.5 degrees, for about 2-5 oscillations. After these oscillations the first oscillation may be restarted or the second oscillation may be started. If the clamping force exceeds the predetermined threshold during the second oscillation, the motor 11 is rotated in the second direction to the initial position and then the first oscillation is restarted. In the event that the predetermined threshold is met multiple times during the first and second oscillations, e.g., about 4 times, the processing unit 54 may fully extend the anvil retainer 30 and provide feedback to a clinician of an error.

Once the second oscillation is completed, the processing unit 54 sends control signals to the motor 11 to resume retraction of the anvil retainer 30 until the anvil assembly 20 is in the clamped position (Step 350). During this retraction, the anvil splines 34 engage the shell splines 36 to clock the anvil assembly 20 with the shell assembly 18 as detailed above.

The Crash Algorithm may reduce the impact of a perceived or actual spline crash allow for clamping of tissue between an anvil assembly 20 and a shell assembly 18 without requiring a signification extension of the anvil assembly 20 away from the shell assembly 18. Additionally, the Crash Algorithm may increase confidence of a clinician during a surgical procedure that tissue is properly clamped between the anvil assembly 20 and the shell assembly 18 before firing of the staples.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A method for obviating spline crash in a surgical stapler utilizing a processing unit in communication with a motor of the surgical stapler, the method comprising:
   oscillating an anvil retainer of the surgical stapler in a longitudinal direction between extension and retraction with the motor such that an anvil of the surgical stapler moves towards and away from a shell assembly of the surgical stapler in a first oscillation pattern;
   oscillating the anvil retainer in the longitudinal direction between extension and retraction such that the anvil moves towards and away from the shell assembly in a second oscillation pattern after the first oscillation pattern;
   retracting the anvil retainer until the anvil is in a clamped position relative to the shell assembly after the second oscillation pattern; and
   the processing unit detecting potential spline crash of an anvil spline of an anvil assembly of the surgical stapler with a shell spline of the shell assembly of the surgical stapler before oscillating the anvil retainer in the first oscillation pattern.

2. The method according to claim 1, wherein oscillating the anvil retainer in the first oscillation pattern including cycling the motor between extending the anvil retainer a first distance and then retracting the anvil retainer the first distance.

3. The method according to claim 2, wherein oscillating the anvil retainer in the first oscillation pattern includes cycling the motor for 5 to 20 cycles before oscillating the anvil retainer in the second oscillation pattern.

4. The method according to claim 2, wherein oscillating the anvil retainer in the second oscillation pattern includes cycling the motor between extending the anvil retainer a second distance and then retracting the anvil retainer a third distance that is greater than the second distance.

5. The method according to claim 4, wherein oscillating the anvil retainer in the second oscillation pattern includes cycling the motor in for 5 to 10 cycles before retracting the anvil retainer until the anvil is in the clamped position.

6. The method according to claim 4, wherein the third distance is equal to the first distance.

7. The method according to claim 4, wherein the second distance is half of the third distance.

8. The method according to claim 2, wherein oscillating the anvil retainer in the second oscillation pattern includes cycling the motor half of the number of cycles the motor is cycled during oscillating the anvil retainer in the first oscillation pattern.

9. The method according to claim 2, wherein oscillating the anvil retainer the first oscillation pattern may include cycling the motor at a frequency in a range of 60 Hz to about 120 Hz.

10. The method according to claim 1, wherein oscillating the anvil retainer in the first oscillation pattern includes cycling the motor to extend the anvil retainer for a first time period and then to retract the anvil retainer for a second time period equal to the first time period.

11. The method according to claim 10, wherein oscillating the anvil retainer in the second oscillation pattern includes cycling the motor includes to extend the anvil retainer for a third time period and then to retract the anvil retainer for a fourth time period greater than the third time period.

12. The method according to claim 11, wherein the third time period is half of the fourth time period.

13. The method according to claim 12, wherein the fourth time period is equal to the first time period.

14. The method according to claim 1, wherein oscillating the motor in the first oscillation pattern and oscillating the motor in the second oscillation pattern includes cycling the motor at the same frequency.

15. A method for obviating spline crash in a surgical stapler utilizing a processing unit in communication with a motor of the surgical stapler, the method comprising:
   oscillating an anvil retainer of the surgical stapler in a longitudinal direction between extension and retraction with the motor such that an anvil of the surgical stapler moves towards and away from a shell assembly of the surgical stapler in a first oscillation pattern;
   oscillating the anvil retainer in the longitudinal direction between extension and retraction such that the anvil moves towards and away from the shell assembly in a second oscillation pattern after the first oscillation pattern;
   retracting the anvil retainer until the anvil is in a clamped position relative to the shell assembly after the second oscillation pattern;
   the processing unit detecting potential spline crash of an anvil spline of an anvil assembly of the surgical stapler with a shell spline of the shell assembly of the surgical stapler after oscillating the anvil retainer in the first oscillation pattern; and
   repeating oscillating the anvil retainer in the first oscillation pattern.

16. A method for obviating spline crash in a surgical stapler utilizing a processing unit in communication with a motor of the surgical stapler, the method comprising:
   oscillating an anvil retainer of the surgical stapler in a longitudinal direction between extension and retraction with the motor such that an anvil of the surgical stapler moves towards and away from a shell assembly of the surgical stapler in a first oscillation pattern;
   retracting the anvil retainer until the anvil is in a clamped position relative to the shell assembly after the first oscillation pattern; and
   the processing unit detecting potential spline crash of an anvil spline of an anvil assembly of the surgical stapler with a shell spline of the shell assembly of the surgical stapler before oscillating the anvil retainer in the first oscillation pattern.

17. The method according to claim 16, wherein oscillation the anvil retainer in the first oscillation pattern includes cycling the motor between extension and retraction for 10 to 20 cycles.

18. A surgical stapler comprising:
   an anvil assembly including an anvil spline;
   a shell assembly including a shell spline; and
   a handle assembly including an anvil retainer, the shell assembly secured to a distal portion of the handle assembly and the anvil assembly secured to the anvil retainer, the handle assembly including a motor configured to extend and retract the anvil retainer through the shell assembly such that the anvil assembly is moved away and towards the shell assembly, the motor configured to oscillate the anvil retainer between extension and retraction in a first oscillation pattern to obviate a spline crash between the anvil spline and the shell spline, the handle assembly including a processing unit in communication with the motor for instructing the motor to perform a spline crash correction algorithm, wherein the spline crash correction algorithm includes:
- oscillating the anvil retainer of the surgical stapler in a longitudinal direction between extension and retraction with the motor such that the anvil of the surgical stapler moves towards and away from the shell assembly of the surgical stapler in the first oscillation pattern;
- oscillating the anvil retainer in the longitudinal direction between extension and retraction such that the anvil moves towards and away from the shell assembly in a second oscillation pattern after the first oscillation pattern;
- retracting the anvil retainer until the anvil is in a clamped position relative to the shell assembly after the second oscillation pattern; and
- detecting potential spline crash of the anvil spline of the anvil assembly of the surgical stapler with the shell spline of the shell assembly of the surgical stapler before oscillating the anvil retainer in the first oscillation pattern.

19. The surgical stapler according to claim 18, wherein the motor is configured to oscillate the anvil retainer between extension and retraction in the second oscillation pattern different from the first oscillation pattern to resume retraction of the anvil assembly relative to the shell assembly after oscillating the anvil retainer in the first oscillation pattern.

* * * * *